(12) United States Patent
Lacy

(10) Patent No.: US 8,795,309 B2
(45) Date of Patent: Aug. 5, 2014

(54) DEVICE FOR INSERTION OF A CANNULA OF AN INFUSION DEVICE AND METHOD

(75) Inventor: Christopher Allen Lacy, Arden Hills, MN (US)

(73) Assignee: Smiths Medical ASD, Inc., Rockland, MA (US)

( * ) Notice: Subject to any disclaimer, the term of this patent is extended or adjusted under 35 U.S.C. 154(b) by 229 days.

(21) Appl. No.: 12/844,402

(22) Filed: Jul. 27, 2010

(65) Prior Publication Data

US 2011/0028982 A1 Feb. 3, 2011

Related U.S. Application Data

(60) Provisional application No. 61/229,466, filed on Jul. 29, 2009.

(51) Int. Cl.
| | |
|---|---|
| *A61B 17/34* | (2006.01) |
| *A61M 31/00* | (2006.01) |
| *A61M 5/158* | (2006.01) |
| *A61M 5/00* | (2006.01) |

(52) U.S. Cl.
CPC .............. *A61M 5/158* (2013.01); *A61M 5/002* (2013.01); *A61M 2005/1581* (2013.01); *A61M 2005/1585* (2013.01); *A61M 2005/1587* (2013.01)
USPC ....................................... 606/185; 604/93.01

(58) Field of Classification Search
USPC .......... 604/158, 264, 11, 272, 403, 411, 6.05, 604/6.06, 44, 46, 198, 165.01, 188, 192, 604/195, 197, 241, 27, 93.01, 164.01, 604/164.08, 164.07, 164.04, 604/288.01–288.04, 167.02; 606/185, 184, 606/181, 167
See application file for complete search history.

(56) References Cited

U.S. PATENT DOCUMENTS

| | | | |
|---|---|---|---|
| 3,547,119 | A | 12/1970 | Hall |
| 4,531,937 | A | 7/1985 | Yates |

(Continued)

FOREIGN PATENT DOCUMENTS

| | | |
|---|---|---|
| DE | 299 05 072 U1 | 9/1999 |
| DE | 202 20 543 U1 | 10/2003 |

(Continued)

OTHER PUBLICATIONS

International Search Report & Written Opinion submitted in PCT/US2010/043350 on Dec. 3, 2010, 12 pages.

(Continued)

*Primary Examiner* — Kathleen Holwerda
*Assistant Examiner* — Jocelin Tanner
(74) *Attorney, Agent, or Firm* — Patterson Thuente Pedersen, P.A.

(57) ABSTRACT

A device for inserting a needle used to introduce a cannula can include a housing including a closed end, an open end, and an arm including a tab extending from the open end, and a sleeve configured to be placed against the patient's skin, the sleeve defining a slot extending along a length of the sleeve, and a barb positioned adjacent to an end of the slot. The slot is sized to receive at least a portion of the arm and the tab of the housing so that the arm and the tab of the housing slides within the slot as the housing is moved relative to the sleeve, and the barb is positioned to engage the tab of the housing to limit movement of the housing relative to the sleeve. The device can also include a threaded portion of the housing extending towards the closed end of the housing.

20 Claims, 19 Drawing Sheets

(56) References Cited

U.S. PATENT DOCUMENTS

| | | | |
|---|---|---|---|
| 4,755,173 A | 7/1988 | Konopka | |
| 4,805,791 A | 2/1989 | Begley | |
| 4,994,042 A | 2/1991 | Vadher | |
| 5,092,853 A | 3/1992 | Couvertier, II | |
| 5,129,884 A | 7/1992 | Dysarz | |
| 5,135,496 A | 8/1992 | Vetter | |
| 5,137,516 A | 8/1992 | Rand | |
| 5,176,650 A | 1/1993 | Haining | |
| 5,176,662 A | 1/1993 | Bartholomew | |
| 5,257,980 A | 11/1993 | Van Antwerp | |
| 5,451,210 A | 9/1995 | Kramer | |
| 5,522,803 A | 6/1996 | Teissen-Simony | |
| 5,545,143 A | 8/1996 | Fischell | |
| 5,573,510 A | 11/1996 | Isaacson | |
| 5,575,777 A | 11/1996 | Cover | |
| 5,584,813 A | 12/1996 | Livingston | |
| 5,591,188 A | 1/1997 | Waisman | |
| 5,676,156 A | 10/1997 | Yoon | |
| 5,738,641 A | 4/1998 | Watson | |
| 5,817,058 A | 10/1998 | Shaw | |
| 5,833,666 A | 11/1998 | Davis | |
| 5,848,990 A | 12/1998 | Cirelli | |
| 5,851,197 A | 12/1998 | Marano | |
| 5,968,011 A | 10/1999 | Larsen | |
| 5,980,506 A | 11/1999 | Mathiasen | |
| 6,017,328 A | 1/2000 | Fischell | |
| 6,056,718 A * | 5/2000 | Funderburk et al. | 604/93.01 |
| 6,056,726 A | 5/2000 | Isaacson | |
| 6,077,244 A | 6/2000 | Botich | |
| 6,086,575 A | 7/2000 | Mejslov | |
| 6,093,172 A | 7/2000 | Funderburk | |
| 6,123,690 A | 9/2000 | Mejslov | |
| 6,159,181 A | 12/2000 | Crossman | |
| 6,293,925 B1 | 9/2001 | Safabash | |
| 6,302,866 B1 | 10/2001 | Marggi | |
| 6,355,021 B1 | 3/2002 | Nielsen | |
| 6,450,992 B1 | 9/2002 | Cassidy, Jr. | |
| 6,520,938 B1 | 2/2003 | Funderburk | |
| 6,572,586 B1 | 6/2003 | Wojcik | |
| 6,579,267 B2 | 6/2003 | Lynch | |
| 6,607,509 B2 | 8/2003 | Bobroff | |
| 6,620,136 B1 | 9/2003 | Pressly, Sr. | |
| 6,685,674 B2 | 2/2004 | Douglas | |
| 6,736,797 B1 | 5/2004 | Larsen | |
| 6,830,562 B2 | 12/2004 | Mogensen | |
| 6,926,694 B2 | 8/2005 | Marano-Ford | |
| 7,018,344 B2 | 3/2006 | Bressler | |
| 7,052,483 B2 | 5/2006 | Wojcik | |
| 7,056,302 B2 | 6/2006 | Douglas | |
| 7,303,543 B1 * | 12/2007 | Maule et al. | 604/93.01 |
| 7,585,287 B2 | 9/2009 | Bresina et al. | |
| 7,699,807 B2 | 4/2010 | Faust | |
| 7,699,808 B2 | 4/2010 | Marrs | |
| 7,731,691 B2 | 6/2010 | Cote | |
| 7,850,658 B2 | 12/2010 | Faust | |
| 7,993,306 B2 | 8/2011 | Marrs et al. | |
| 2001/0053889 A1 | 12/2001 | Marggi | |
| 2002/0045867 A1 | 4/2002 | Nielsen | |
| 2002/0077599 A1 | 6/2002 | Wojcik | |
| 2002/0161332 A1 | 10/2002 | Ramey | |
| 2002/0173769 A1 | 11/2002 | Gray | |
| 2003/0014018 A1 | 1/2003 | Giambattista | |
| 2003/0060781 A1 | 3/2003 | Mogensen | |
| 2003/0109829 A1 | 6/2003 | Mogensen | |
| 2003/0125669 A1 | 7/2003 | Safabash | |
| 2003/0130619 A1 | 7/2003 | Safabash | |
| 2003/0158520 A1 | 8/2003 | Safabash | |
| 2003/0199823 A1 | 10/2003 | Bobroff | |
| 2003/0225373 A1 | 12/2003 | Bobroff | |
| 2003/0225374 A1 | 12/2003 | Mathiasen | |
| 2004/0002682 A1 | 1/2004 | Kovelman | |
| 2004/0143216 A1 | 7/2004 | Douglas | |
| 2004/0158207 A1 * | 8/2004 | Hunn et al. | 604/164.01 |
| 2004/0199123 A1 | 10/2004 | Nielsen | |
| 2004/0204687 A1 | 10/2004 | Mogensen | |
| 2004/0215151 A1 | 10/2004 | Marshall | |
| 2004/0236284 A1 | 11/2004 | Hoste | |
| 2004/0260250 A1 | 12/2004 | Harris | |
| 2005/0043687 A1 | 2/2005 | Mogensen | |
| 2005/0075606 A1 | 4/2005 | Botich | |
| 2005/0101912 A1 | 5/2005 | Faust | |
| 2005/0101932 A1 | 5/2005 | Cote | |
| 2005/0101933 A1 | 5/2005 | Marrs | |
| 2005/0107743 A1 | 5/2005 | Fangrow | |
| 2005/0113761 A1 | 5/2005 | Faust | |
| 2005/0131346 A1 | 6/2005 | Douglas | |
| 2005/0283114 A1 * | 12/2005 | Bresina et al. | 604/93.01 |
| 2006/0041224 A1 | 2/2006 | Jensen | |
| 2006/0129090 A1 | 6/2006 | Moberg et al. | |
| 2006/0173413 A1 | 8/2006 | Fan | |
| 2008/0103450 A1 | 5/2008 | Marrs et al. | |
| 2008/0243051 A1 | 10/2008 | DeStefano | |
| 2009/0124979 A1 * | 5/2009 | Raymond et al. | 604/195 |
| 2009/0264825 A1 | 10/2009 | Cote | |
| 2009/0287153 A1 | 11/2009 | Bresina et al. | |
| 2012/0179106 A1 | 7/2012 | Cote et al. | |
| 2013/0012881 A1 | 1/2013 | Lacy | |

FOREIGN PATENT DOCUMENTS

| | | |
|---|---|---|
| EP | 0 290 176 A1 | 11/1988 |
| EP | 0 239 244 B1 | 9/1991 |
| EP | 0 451 040 A1 | 10/1991 |
| EP | 0 615 768 B1 | 12/1999 |
| WO | WO 96/32981 | 10/1996 |
| WO | WO 02/081012 A2 | 10/2002 |
| WO | WO 02/100467 A2 | 12/2002 |
| WO | WO 02/102442 A1 | 12/2002 |

OTHER PUBLICATIONS

International Search Report and Written Opinion of the International Searching Authority, mailed Dec. 3, 2010, 12 pages.

Application and File History for U.S. Appl. No. 13/619,396 filed Sep. 14, 2012, inventor Lacy.

* cited by examiner

DEVICE FOR INSERTION OF A CANNULA OF AN INFUSION DEVICE AND METHOD

RELATED APPLICATION

This application claims the benefit of U.S. patent application Ser. No. 61/229,466 filed on Jul. 29, 2009, the entirety of which is hereby incorporated by reference.

BACKGROUND

Infusion devices are used to deliver substances such as medications into the subcutaneous layer of skin of a patient. Devices for assisting in insertion of the cannula of an infusion device into the skin of the patient are known. For example, some devices utilize springs to automatically drive a needle into the skin of a patient to introduce the cannula of the infusion device into the subcutaneous layer.

Because a needle is used to introduce the cannula of the infusion device into the subcutaneous layer of skin, there is a risk associated with inadvertent exposure to the needle. Further, patients may react adversely to viewing the needle prior to insertion and may, for example, be reluctant to place the needle into the skin. Prior devices may not adequately shroud this needle prior to and/or after introduction of the infusion device.

Other issues of concern in the design and use of insertion devices include ease of use by the patient and sterilization. For example, some patients may have difficulty loading the infusion device into the insertion device.

SUMMARY

In one aspect, a device for inserting a needle used to introduce a cannula of a subcutaneous infusion device into a subcutaneous layer of skin of a patient includes: a housing including a closed end, an open end, and an arm including a tab extending from the open end; and a sleeve configured to be placed against the patient's skin to introduce the cannula into the patient's skin, the sleeve defining a slot extending along a length of the sleeve, and a barb positioned adjacent to an end of the slot; wherein the slot is sized to receive at least a portion of the arm and the tab of the housing so that the arm and the tab of the housing slides within the slot as the housing is moved relative to the sleeve; and wherein the barb is positioned to engage the tab of the housing to limit movement of the housing relative to the sleeve.

In another aspect, a device for inserting a needle used to introduce a cannula of a subcutaneous infusion device into a subcutaneous layer of skin of a patient includes: a housing including a closed end, an open end, and defining an internal cavity, the housing including a threaded portion positioned adjacent to the open end, the threaded portion extending towards the closed end of the housing; the needle positioned within the internal cavity of the housing and coupled to the cannula of the subcutaneous infusion device; a cap including a cap closed end and a cap open end, the cap including a cap threaded portion positioned adjacent to the open end; wherein the cap threaded portion is coupled to the threaded portion of the housing with the device in a ship state.

In another aspect, a method for inserting a needle used to introduce a cannula of a subcutaneous infusion device into a subcutaneous layer of skin of a patient includes: positioning a tab of a housing in a slot formed by a sleeve of a device; positioning the sleeve against the patient's skin; moving the housing relative to the sleeve to introduce the cannula into the patient's skin; and allowing the tab to slide within the slot as the housing is moved relative to the sleeve.

DETAILED DESCRIPTION

Figure 1:
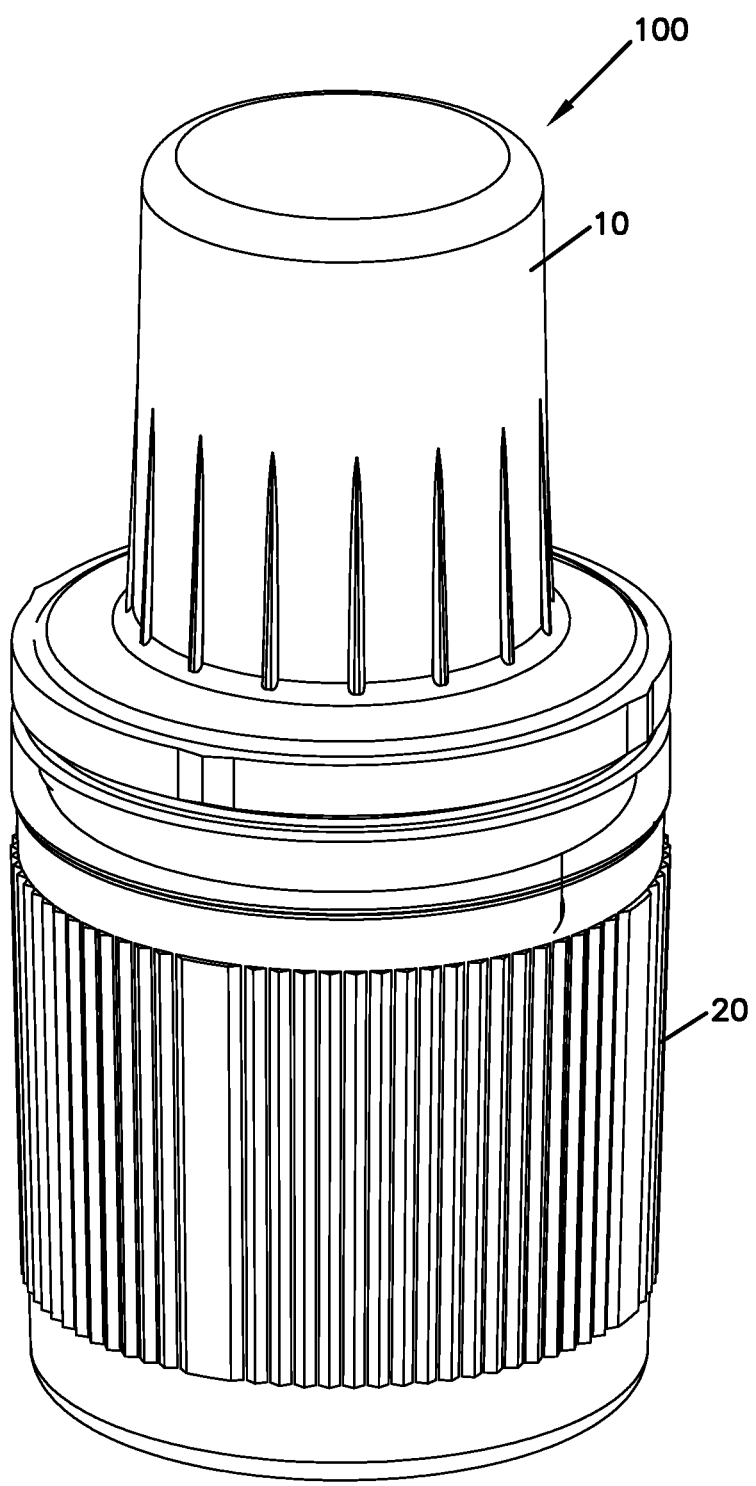
FIG. 1 is a perspective view of an example embodiment of a device used to introduce a cannula of an infusion device into a patient.

A first embodiment of a device 100 is shown in FIGS. 1-17. As shown in FIG. 10, the device 100 includes a housing 10, a needle hub 1, a cylinder hub 2, a spring 3, a sleeve 15, a site 6 including a septum 5, a holder 4, and an adhesive layer 7, and a removable cap 20.

Generally, the device 100 is used to introduce a cannula 50 associated with the site 6 into the skin of a patient. The site 6 is then disconnected from the device 100, and the site 6 remains on the skin to deliver substances to the patient.

The housing 10 is preferably cylindrical in shape and includes a closed upper end and an open lower end. The housing 10 further preferably includes a knurled exterior surface to enhance a patient's grip on the housing 10, as well as a threaded portion 11 positioned to engage the cap 20, as described further below. The housing 10 includes an internal cavity sized to receive at least a portion of the needle hub 1 and the cylinder hub 2.

The needle hub 1 includes a main body 201 and a needle 202 (hollow or solid) coupled to the main body 201. The needle hub 1 is positioned in the interior passage of the cylinder hub 2 in a fixed position relative to the cylinder hub 2 and the housing 10. See, for example, FIGS. 3, 6, 9.

The cylinder hub 2 is coupled to the upper end of the housing 10. The cylinder hub 2 includes the interior passage into which the needle hub 1 is positioned. As described further below, the needle hub 1 moves longitudinally within the passage formed by the cylinder hub 2.

Figure 3:
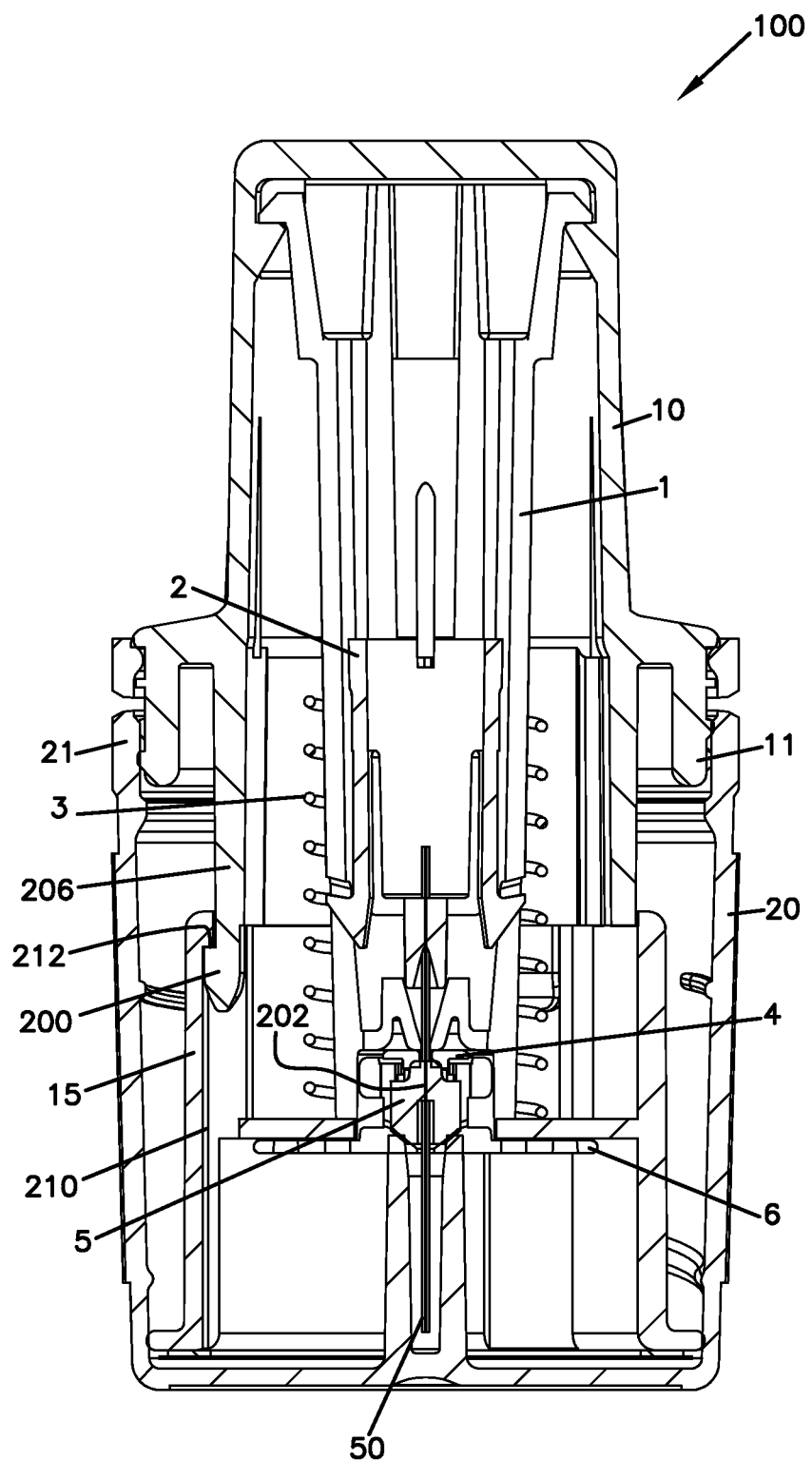
FIG. 3 is a cross-sectional view taken along line A-A of the device of FIG. 2.
Figure 6:
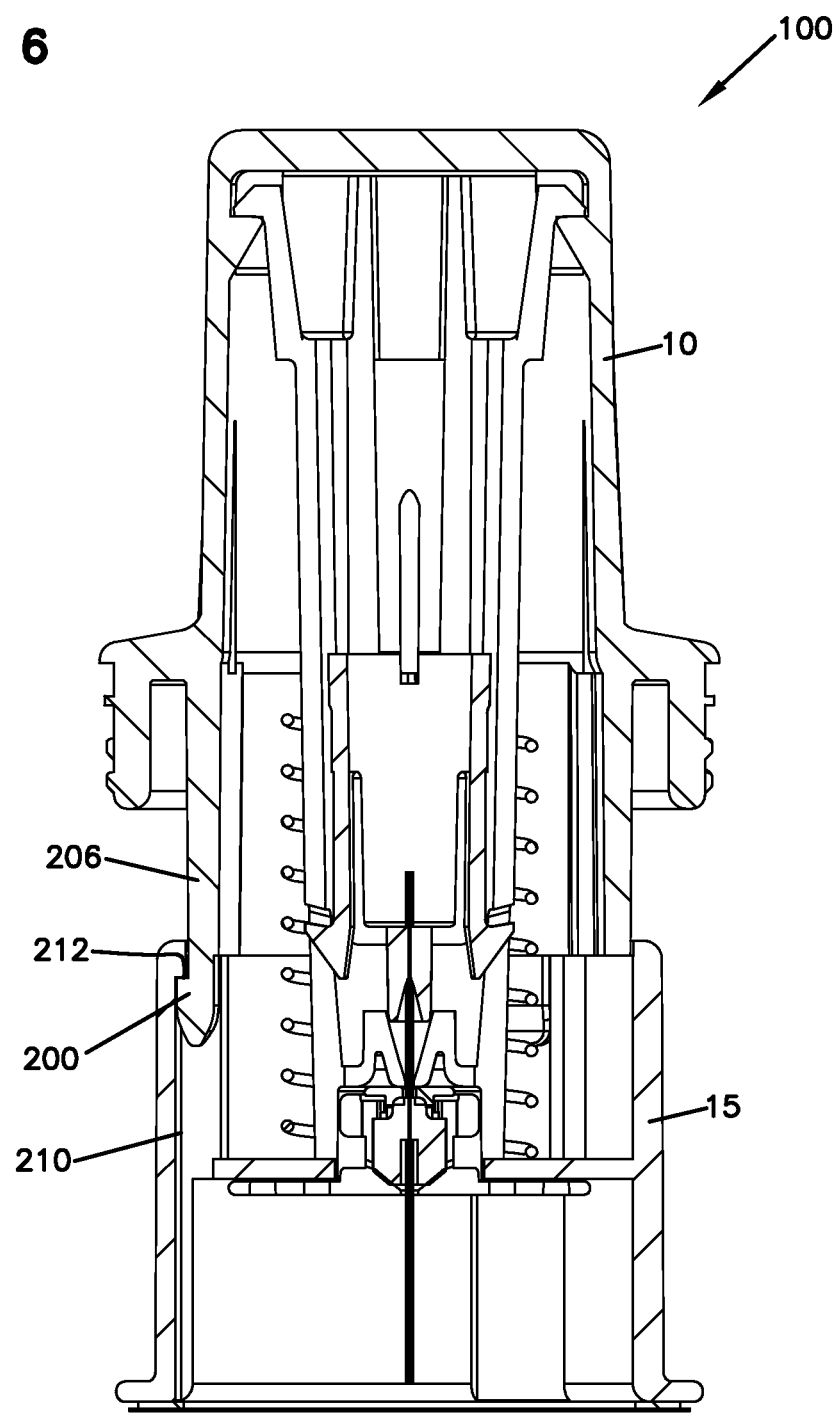
FIG. 6 is a cross-sectional view taken along line B-B of the device of FIG. 5.

The spring 3 surrounds a portion of the cylinder hub 2. One end of the spring 3 is seated on the sleeve 15, and the other end of the spring 3 engages the needle hub 1. The spring 3 is in a compressed state as shown in FIGS. 3 and 6 and therefore applies force against the needle hub 1, biasing the needle hub 1 in an upward direction towards the closed end of the housing 10. Likewise, the spring 3 forces the housing 10 and the sleeve 15 apart. Further, as the housing 10 and associated needle hub 1 are moved relative to the sleeve 15, the spring 3 is further compressed until the needle hub 1 is released from the cylinder hub 2, as described below. At that point, the spring 3 forces the needle hub 1 back upward into the housing 10.

The sleeve 15 is preferably cylindrical in shape. The sleeve 15 is coupled to the housing 10 such that the housing 10 can be moved longitudinally with respect to the sleeve 15, as described herein.

The site 6 is loaded into the device 100 prior to application of the adhesive layer 7 onto the device 100. The adhesive layer 7 is pierced by the needle 202 as the needle 202 is advanced towards the skin, as described further below. The adhesive layer 7 maintains the site 6 on the skin of the patient. The site 6 includes the septum 5 that is piercable by a needle of a set configured to deliver medication into the septum 5, through the cannula 50, and into the patient. The holder 4 maintains the septum 5 in position within the site 6.

The cap 20 includes a closed end and an open end. The cap 20 preferably includes an exterior with a knurled surface to enhance the patient's grip on the cap 20. In addition, the interior of the cap 20 includes a threaded portion 21 positioned adjacent the open end so that the threaded portion 21 can be threaded onto the threaded portion 11 of the housing 10 to seal the device 100. See FIGS. 1-3.

Figure 7:
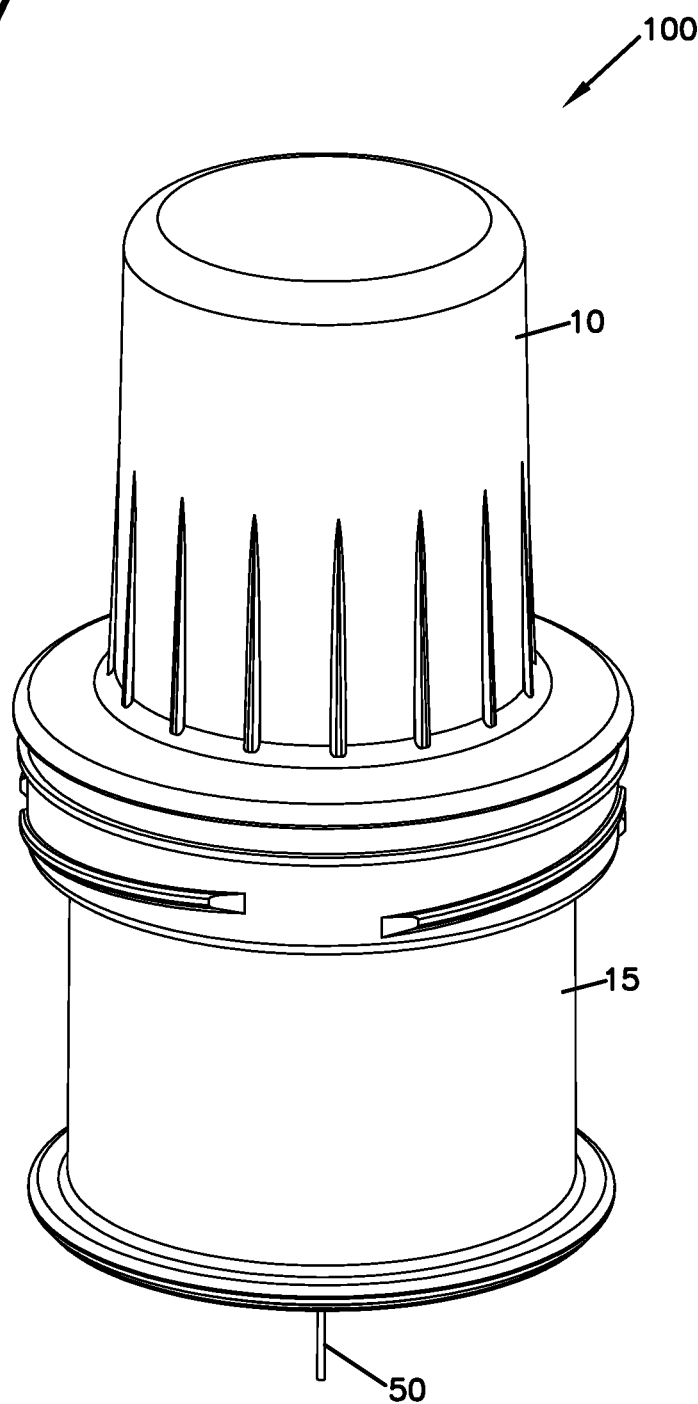
FIG. 7 is a perspective view of the device of FIG. 3 in a trigger state.
Figure 8:
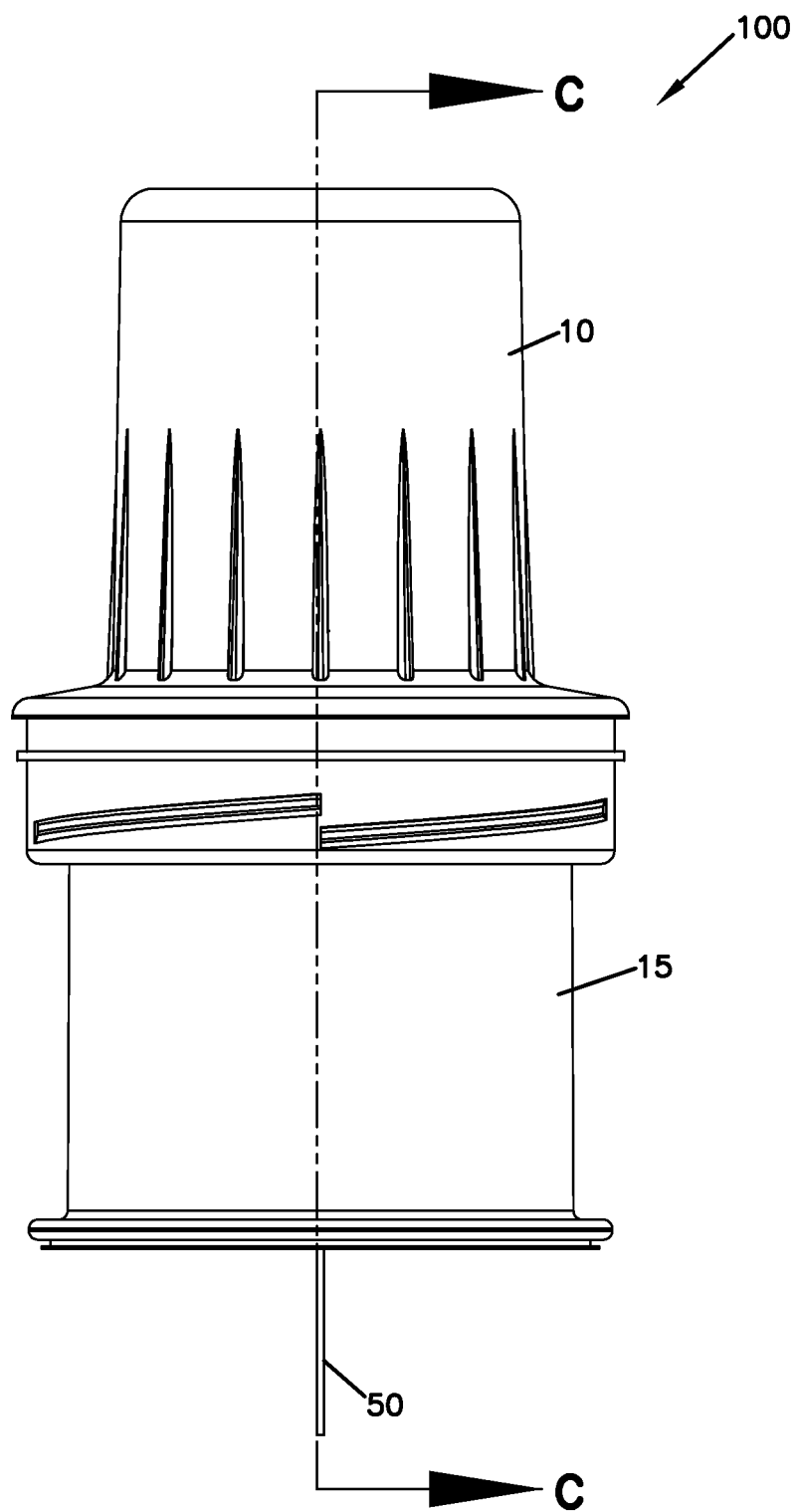
FIG. 8 is a side view of the device of FIG. 7.
Figure 9:
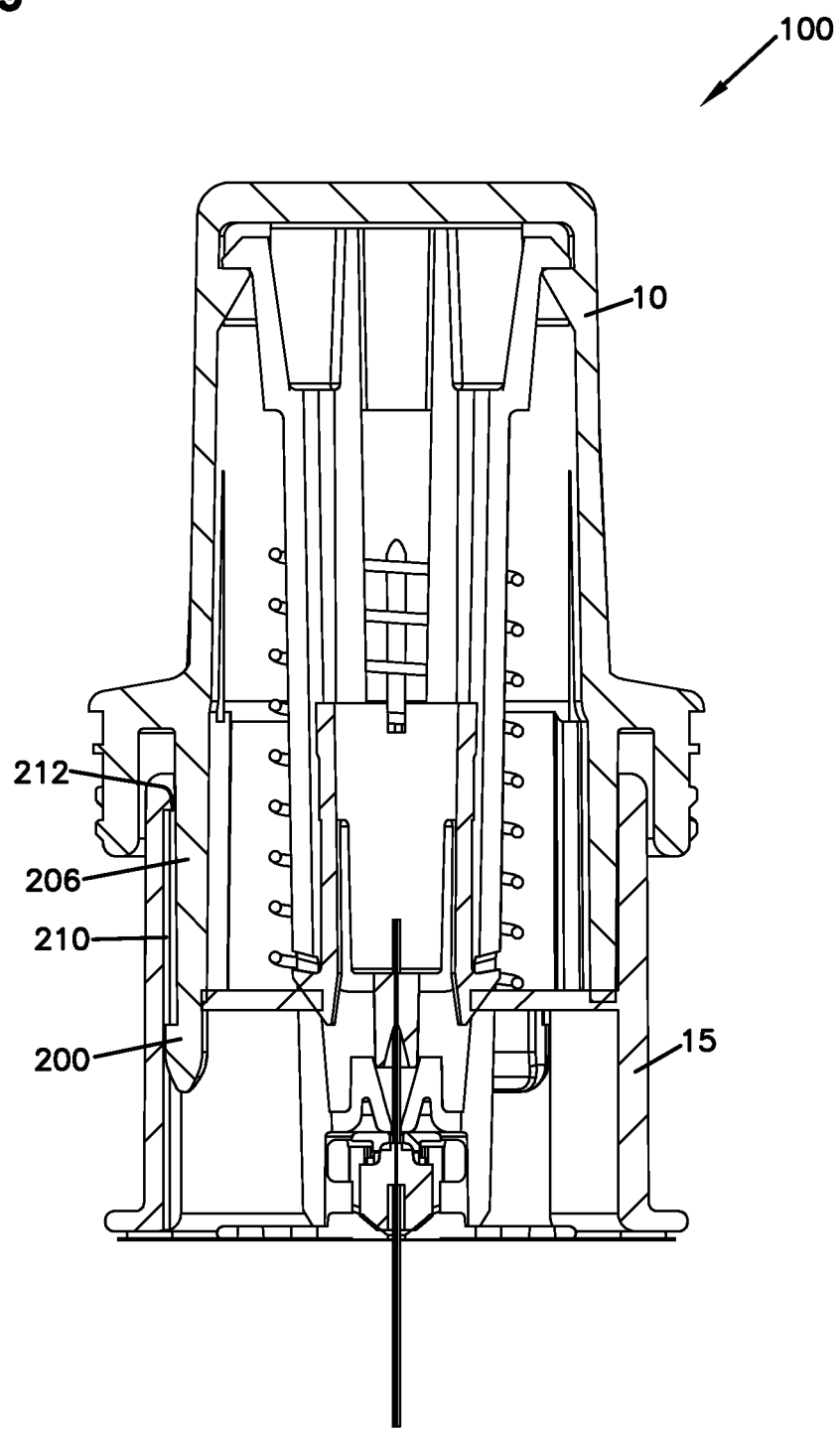
FIG. 9 is a cross-sectional view taken along line C-C of the device of FIG. 8.
Figure 10:
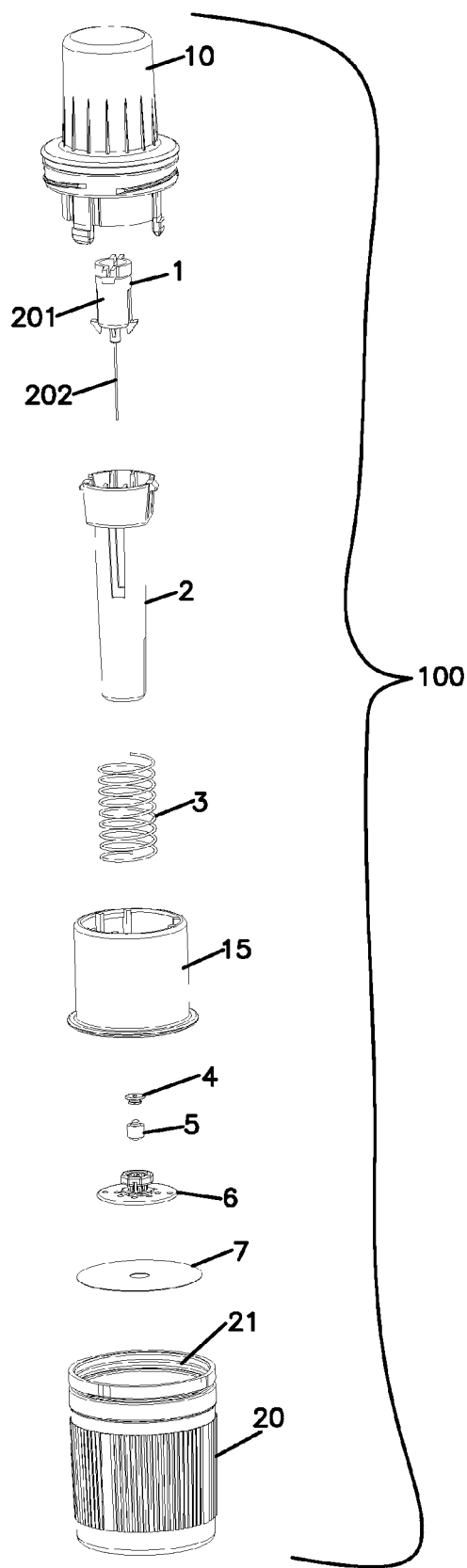
FIG. 10 is an exploded view of the device of FIG. 1.

As shown in FIGS. 1-9, the device 100 includes a ship state (FIGS. 1-3), a delivery state (FIGS. 4-6), and a trigger state (FIGS. 7-9).

Figure 2:
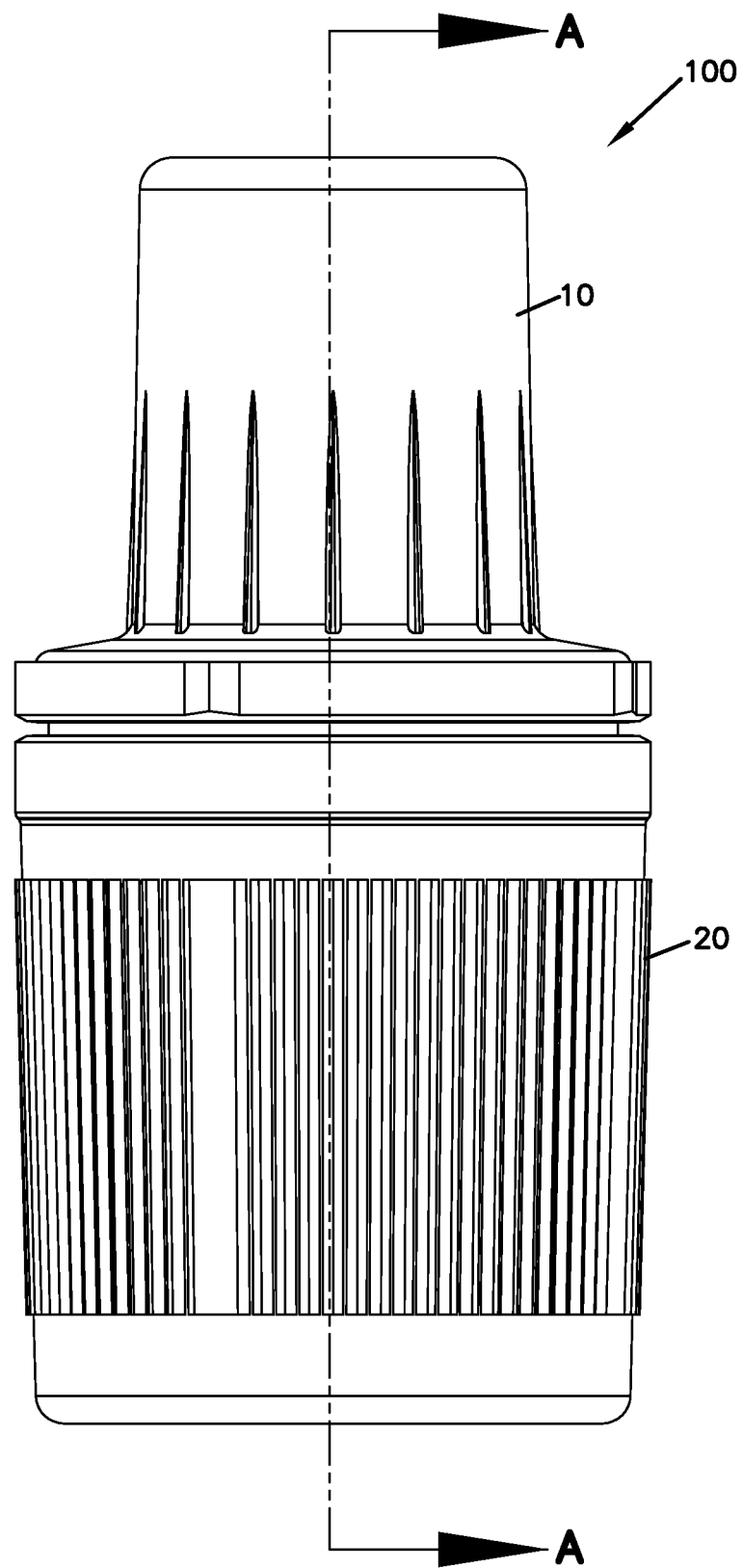
FIG. 2 is a side view of the device of FIG. 1.

In the ship state shown in FIG. 1-3, the device 100 includes the site 6 in a state such that the site 6 is ready for deployment by the patient after the cap 20 is removed.

Figure 4:
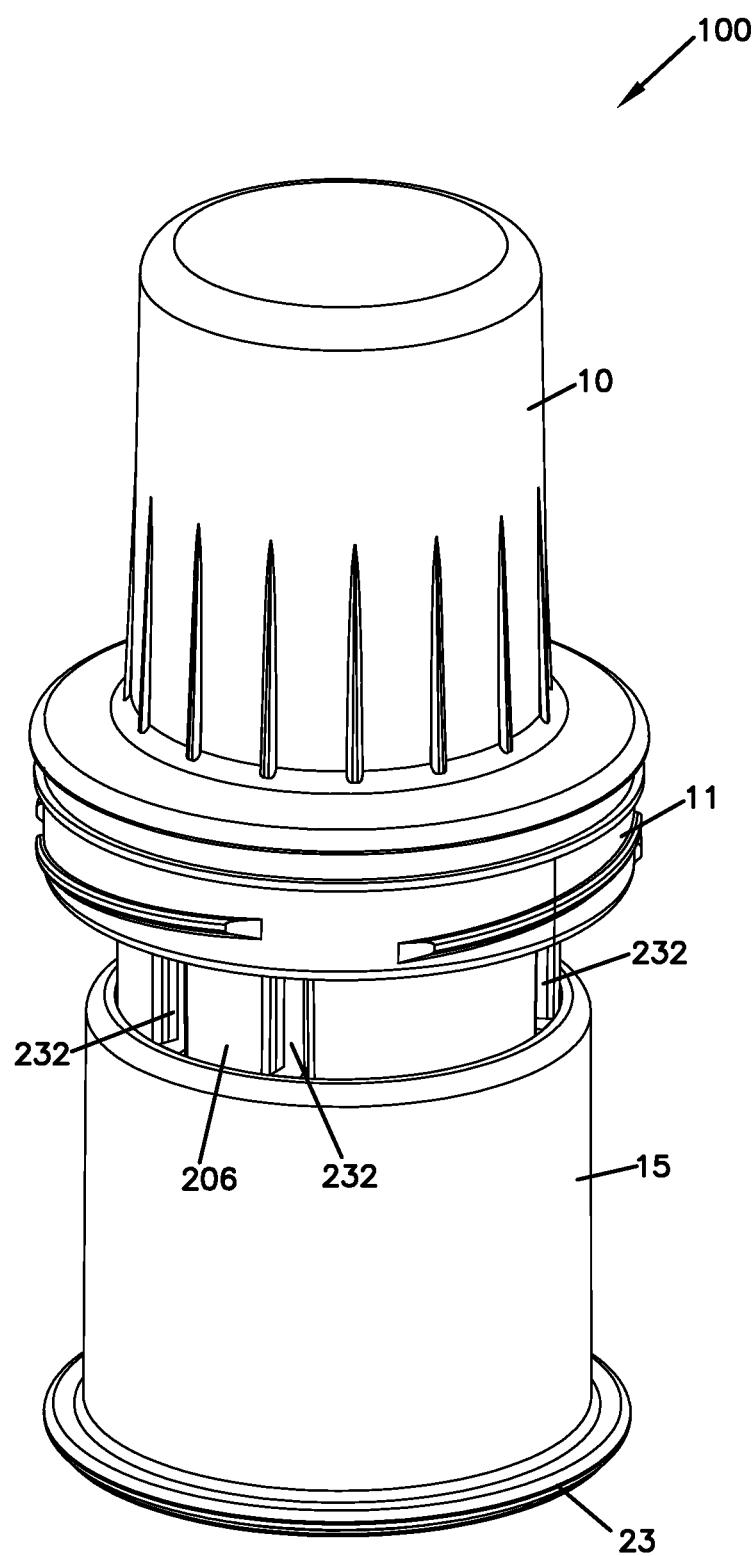
FIG. 4 is a perspective view of the device of FIG. 1 with a cap removed.
Figure 5:
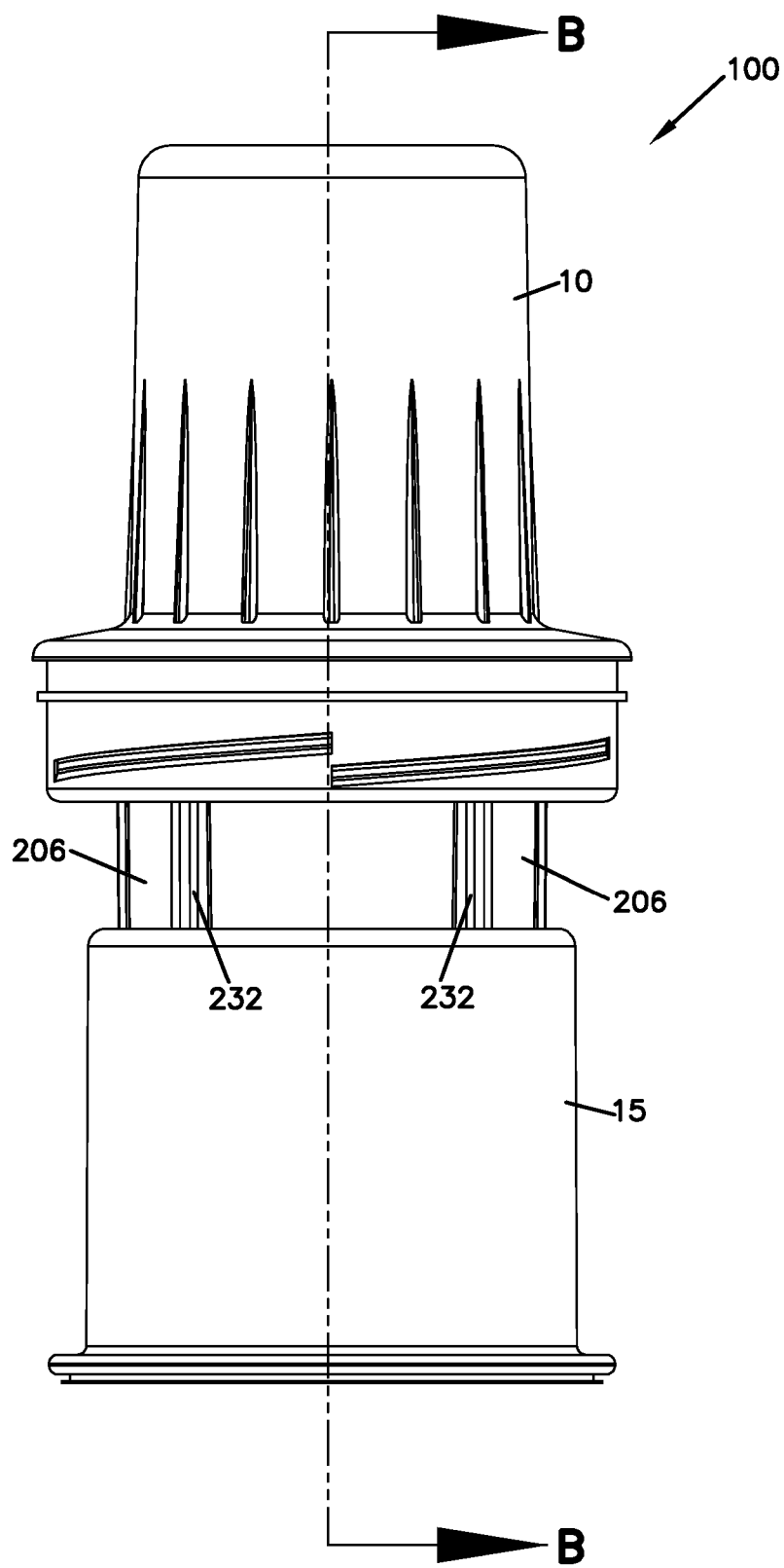
FIG. 5 is a side view of the device of FIG. 4.

In the delivery state shown in FIG. 4-6, the cap 20 has been unscrewed to remove the cap 20 from the device 100. The patient then places an end 23 of the sleeve 15 against the patient's skin at the desired location. In this state, the patient can insert the cannula 50 of the site 6 into the patient's skin. To accomplish this, the needle hub 1 includes the needle 202 that extends through the cannula 50 of the site 6 by depressing the housing 10 to move the needle hub 1 that is coupled thereto so that the needle 202 and associated cannula 50 of the site 6 are introduced into the skin.

In the trigger state shown in FIG. 7-9, the housing 10 has been moved towards the skin until the cannula 50 is fully inserted and the housing 10 has moved adjacent to the sleeve 15. At this state, the spring 3 of the device 100 moves the needle hub up into the housing 10, so that the needle is removed from the skin while leaving the cannula 50 of the site 6 in the skin.

The device 100 can then be removed from the skin and discarded.

Figure 11:
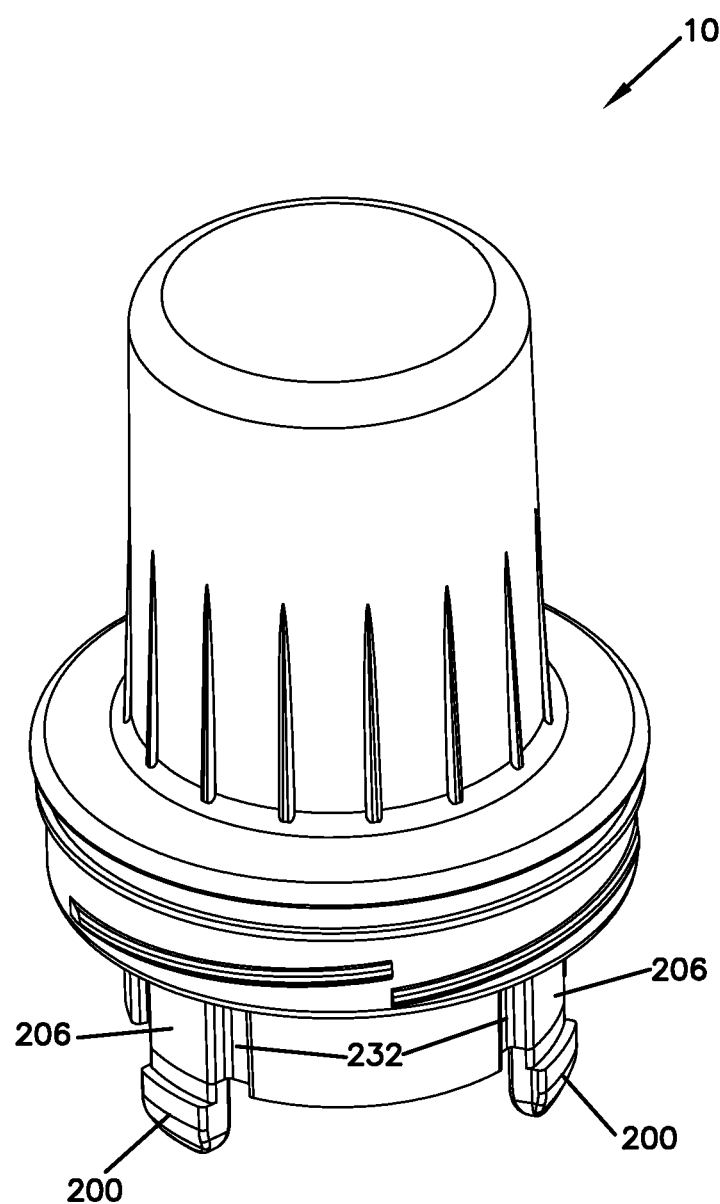
FIG. 11 is a perspective view of an example housing of the device of FIG. 1.
Figure 12:
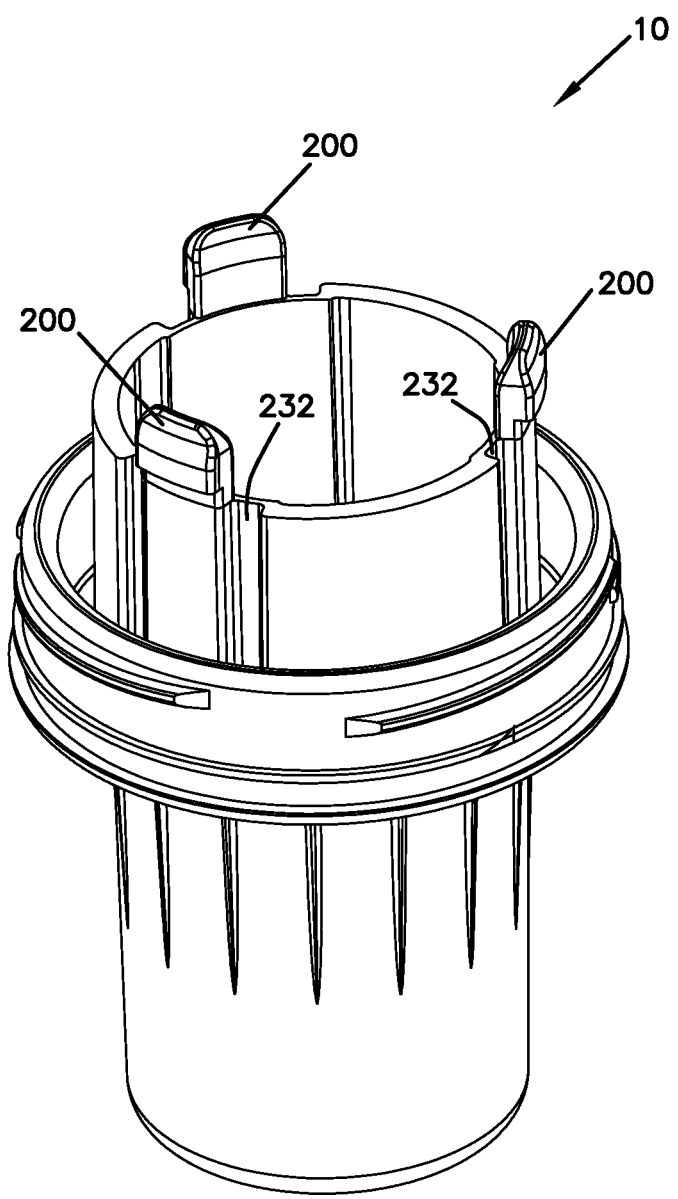
FIG. 12 is another perspective view of the housing of FIG. 11.
Figure 13:
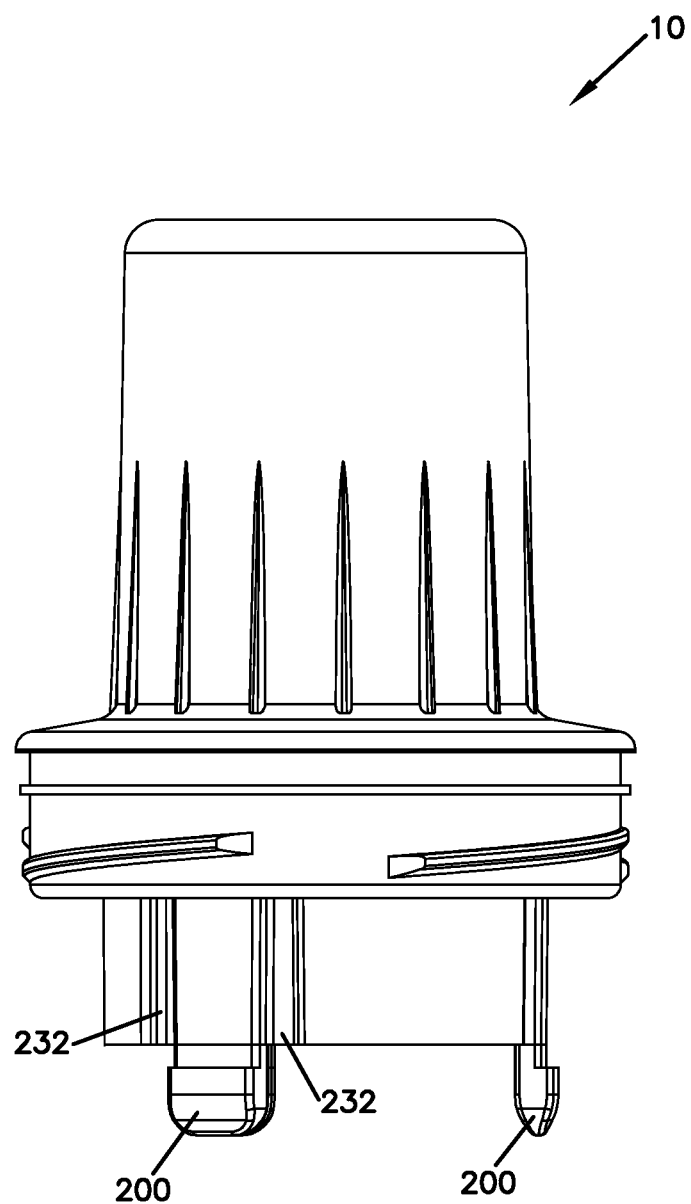
FIG. 13 is a side view of the housing of FIG. 11.
Figure 14:
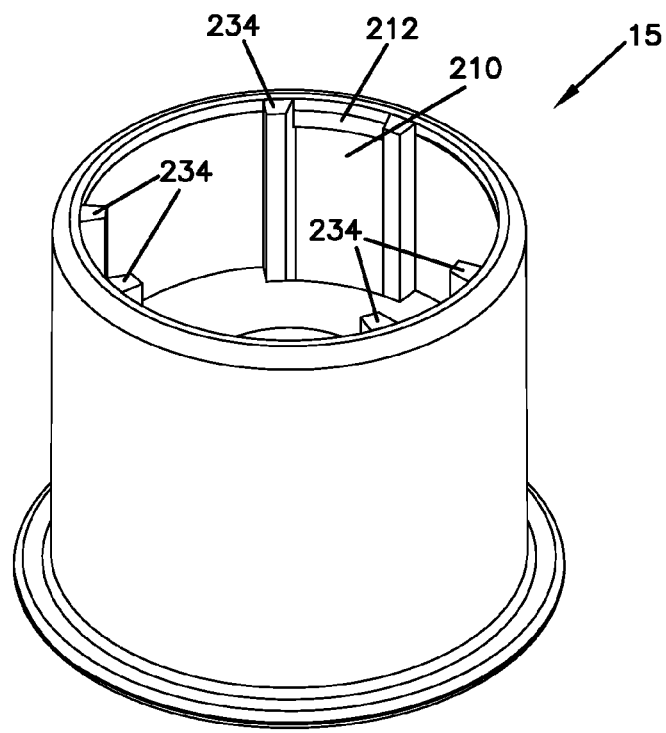
FIG. 14 is a perspective view of an example sleeve of the device of FIG. 1.
Figure 15:
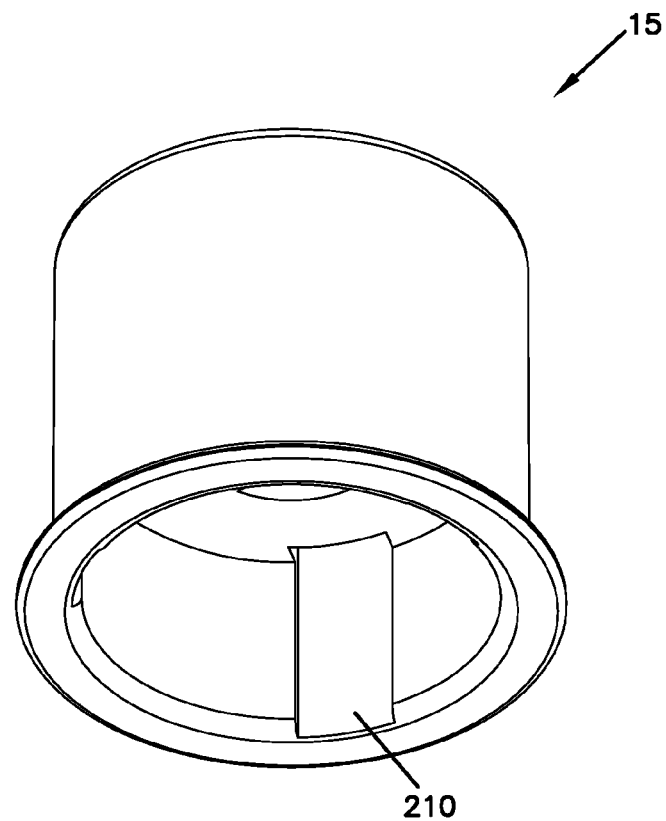
FIG. 15 is another perspective view of the sleeve of FIG. 14.
Figure 17:
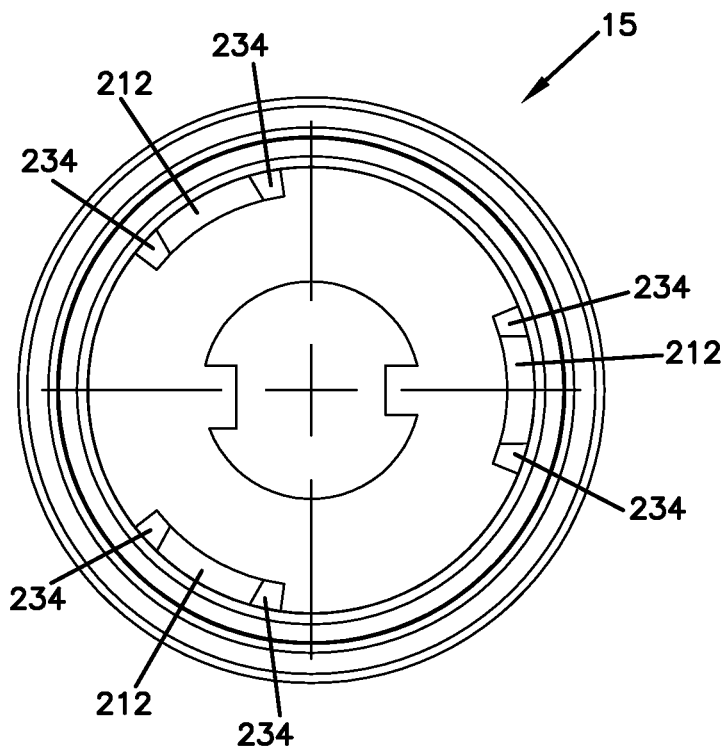
FIG. 17 is an end view of the sleeve of FIG. 14.
Figure 16:
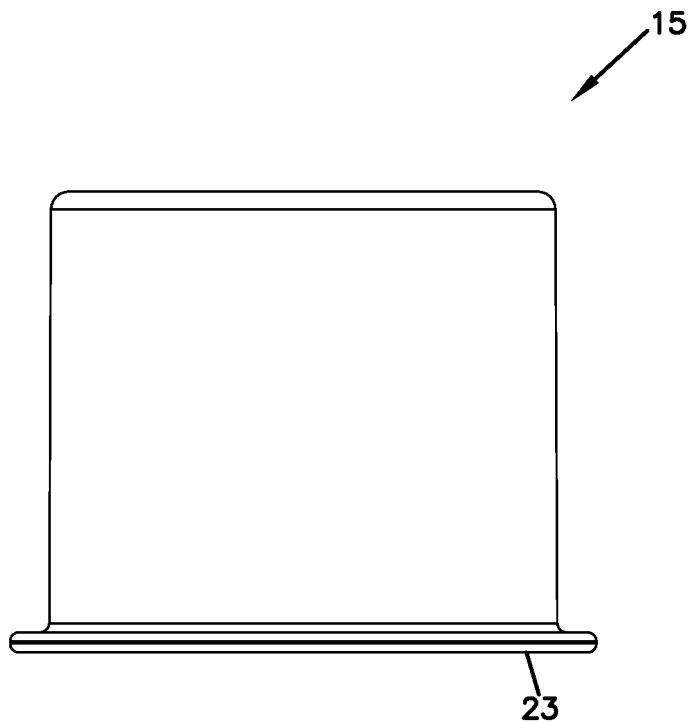
FIG. 16 is a side view of the sleeve of FIG. 14.
Figure 18:
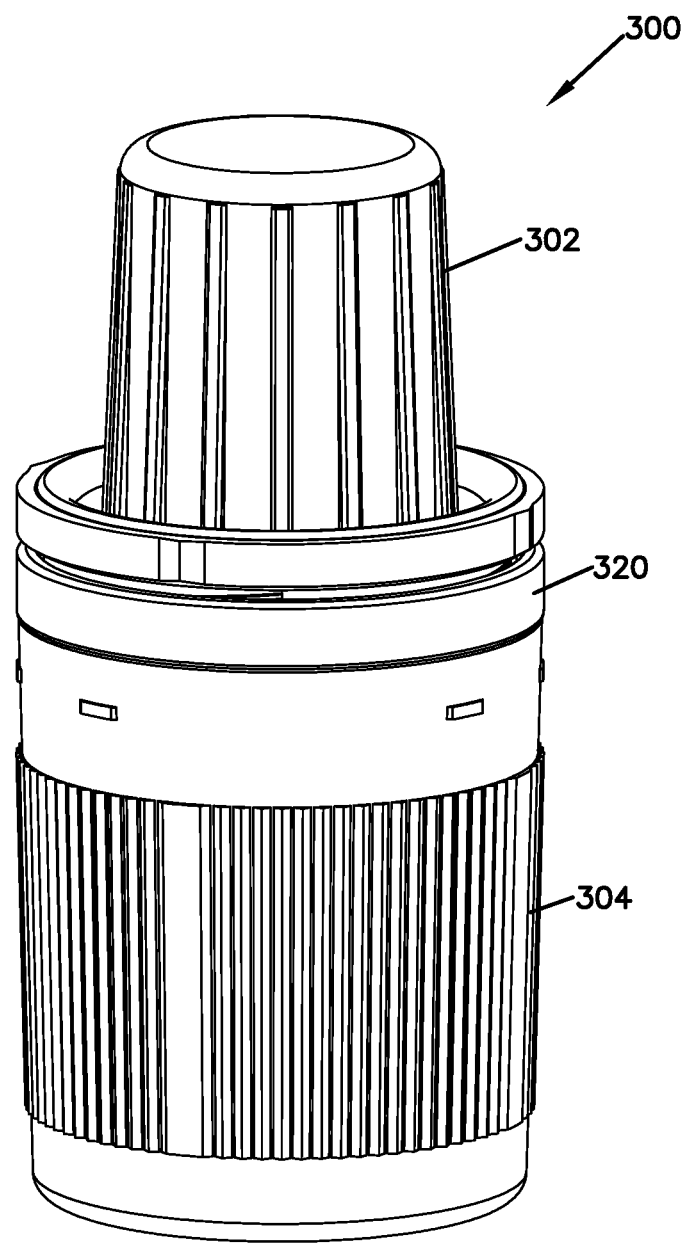
FIG. 18 is a perspective view of another example embodiment of a device used to introduce a cannula of an infusion device into a patient.
Figure 19:
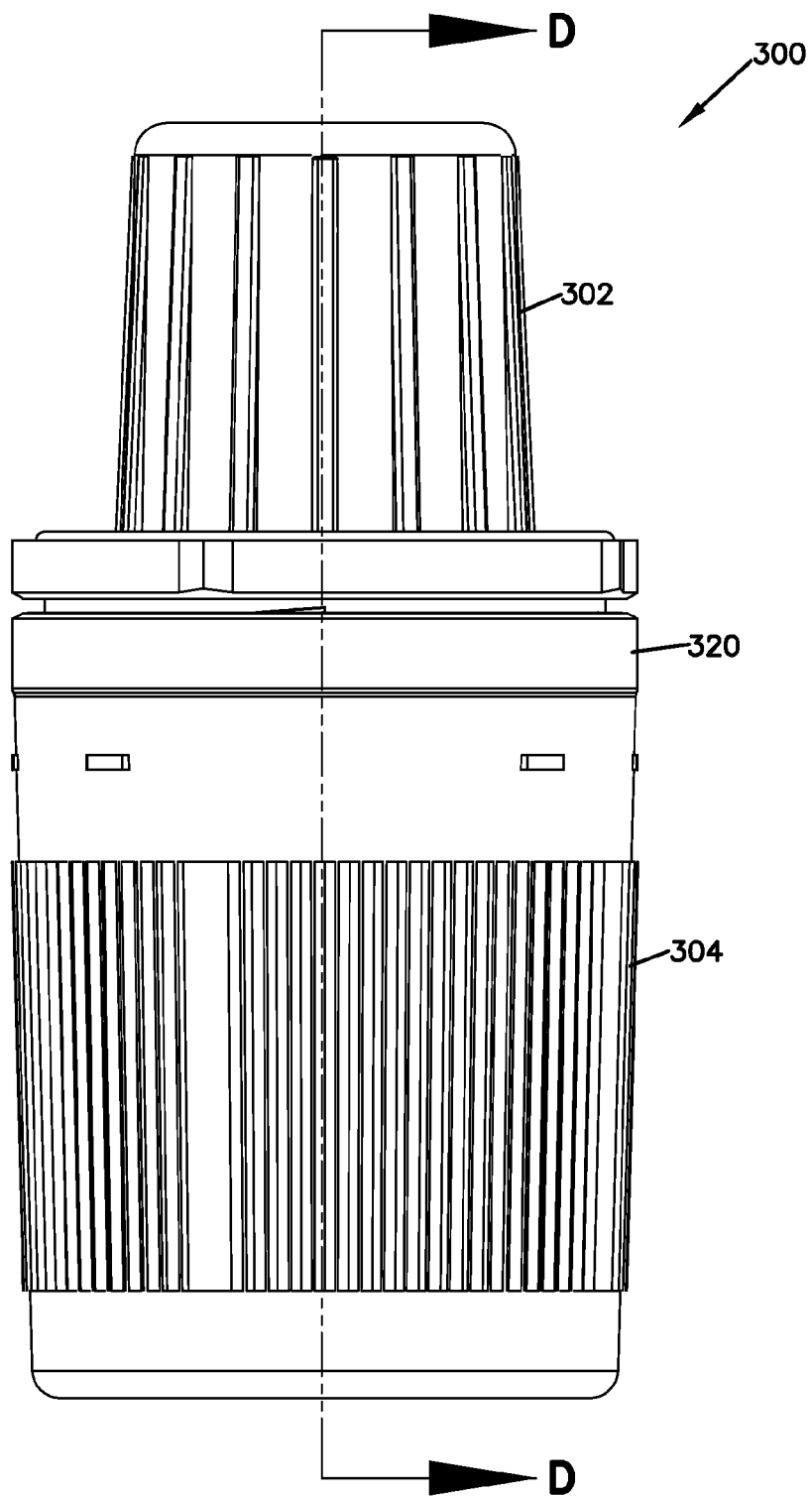
FIG. 19 is a side view of the device of FIG. 18.
Figure 20:
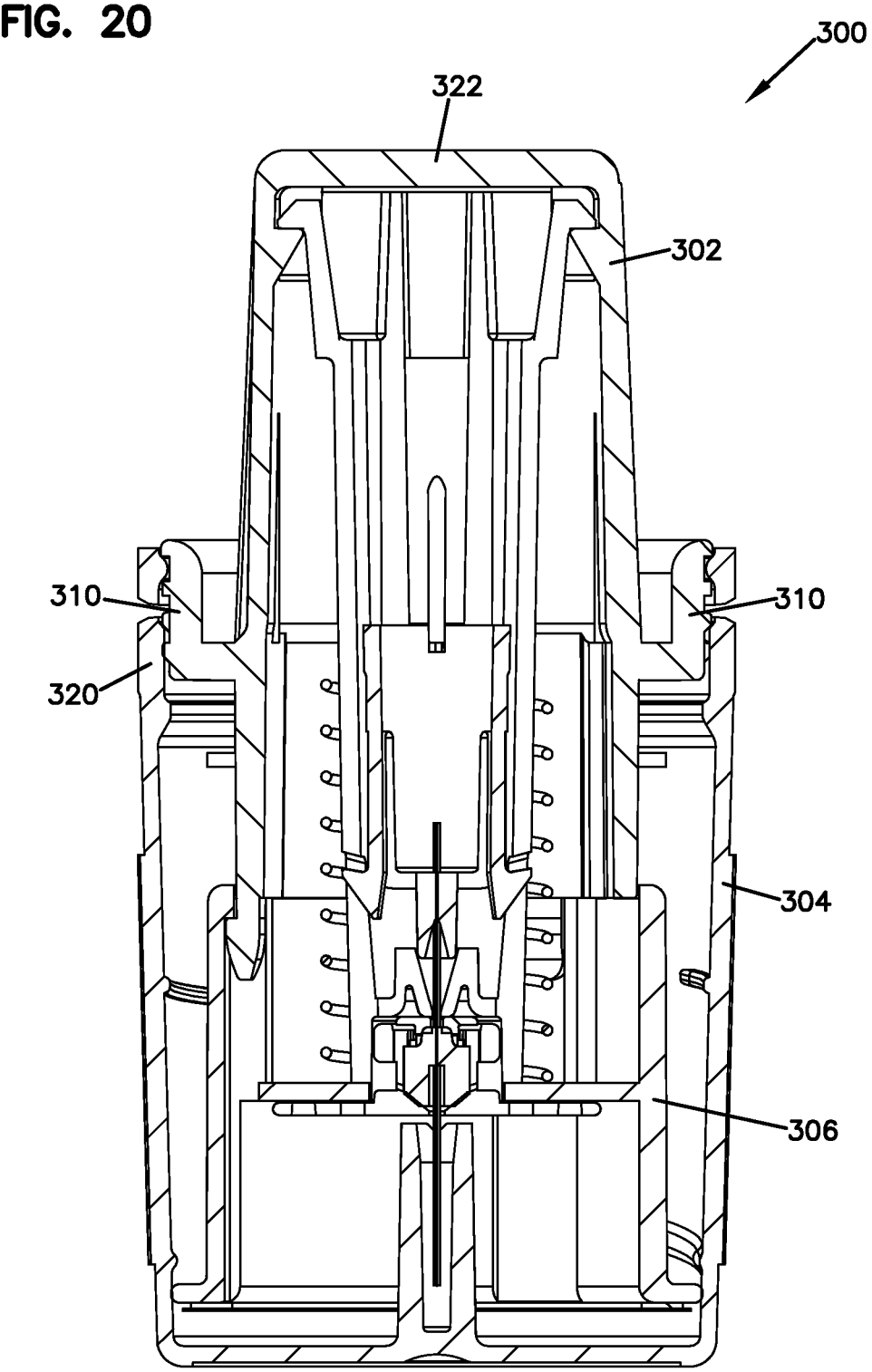
FIG. 20 is a cross-sectional view taken along line D-D of the device of FIG. 19.
Figure 21:
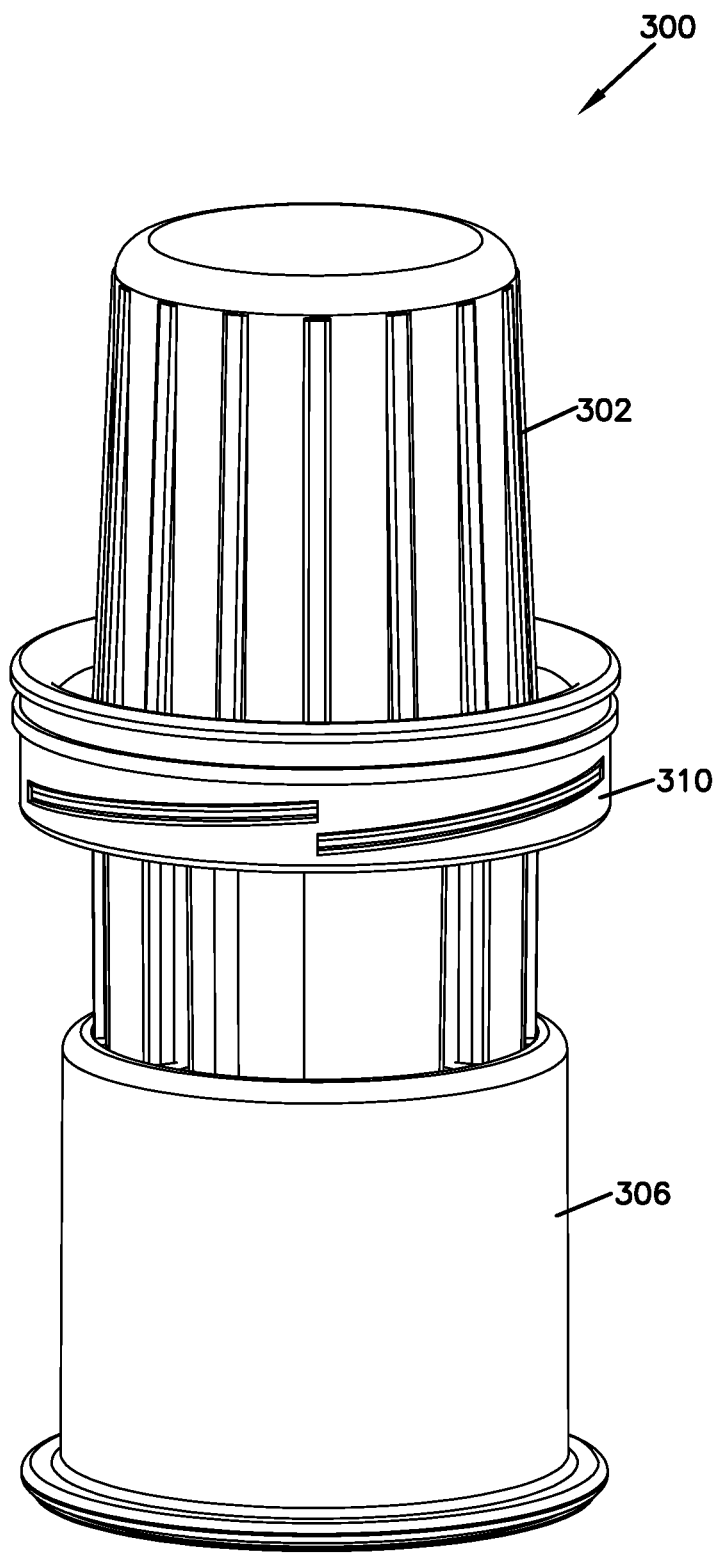
FIG. 21 is a perspective view of the device of FIG. 18 with a cap removed.

As shown in FIGS. 11-13, the housing 10 has three tabs 200 that extend from arms 206 of the housing 10 that engage complementary slots 210 formed along lengths of the sleeve 15 (see FIGS. 14-17) to couple the housing 10 to the sleeve 15. The tabs 200 maintain the connection between the housing 10 and the sleeve 15 while allowing the housing 10 to slide relative to the sleeve 15 in the slots 210 during insertion of the needle and cannula 50 of the site 6 into the skin. At the upper end of each of the slots 210, a barb 212 is formed so that each respective tab 200 engages the barb 212 as the tab 200 slides within the slot 210 to maintain the tab 200 within the slot. See FIGS. 3 and 6.

In addition, in some embodiments, the sleeve 15 includes one or more rails 234 (see FIGS. 14 and 17) that run parallel to the centerline of the sleeve 15 and are positioned adjacent to the slots 210. The rails 234 align with corresponding grooves 232 in the housing 10 (see FIGS. 11-13), so that the rails 234 slide within the grooves 232 during insertion of the needle and cannula 50 of the site 6 into the skin. The engagement of the rails 234 with the grooves 232 maintains the orientation of the housing 10 relative to the sleeve 15 as the housing 10 is slid relative to the sleeve 15 during insertion of the cannula 50. In the example shown, the rails 234 are provided in pairs adjacent to the edges of the slots 210. Other configurations are possible.

Referring now to FIGS. 18-21, another device 300 is shown. The device 300 is similar to the device 100 described above. However, the device 300 includes a housing 302 with a threaded portion 310 that is positioned external from the housing 302 and extends towards a closed end 322 of the housing and away from the sleeve 306, rather than towards the sleeve 306 as shown in the previous embodiment. See FIGS. 20 and 21. In addition, a cap 304 includes an extended portion 320 positioned to be screwed onto the threaded portion 310 of the housing 302.

Additional details regarding some of the components of the devices described herein can be found in U.S. patent application Ser. No. 10/705,719 filed Nov. 10, 2003 and granted as U.S. Pat. No. 7,731,691 on Jun. 8, 2010, the entirety of which is hereby incorporated by reference.

Modifications, permutations, or subsets can be made to the examples described herein without departing from the scope and spirit of the designs.

What is claimed is:

1. A device for inserting a needle used to introduce a cannula of a subcutaneous infusion device into a subcutaneous layer of skin of a patient, the device comprising:
   a housing including a closed end, an open end, and defining an internal cavity, the housing including a threaded portion positioned adjacent to the open end, the threaded portion extending towards the closed end of the housing;
   a sleeve configured to be placed against the patient's skin to introduce the cannula into the patient's skin, the sleeve defining a slot extending along a length of the sleeve, at least one rail extending parallel to a centerline of the sleeve on the same surface as the slot, and a barb positioned adjacent to an end of the slot;
   the needle positioned within the internal cavity of the housing and coupled to the cannula of the subcutaneous infusion device; and
   a cap including a cap closed end and a cap open end, the cap including a cap threaded portion positioned adjacent to the cap open end;
   wherein the cap threaded portion is coupled to the threaded portion of the housing with the device in a ship state, wherein the rail and the slot are immediately adjacent one another on the same surface.

2. The device of claim 1, wherein the threaded portion of the housing is positioned externally.

3. The device of claim 1, wherein the housing further includes an arm including a tab extending from the open end, wherein the slot is sized to receive at least a portion of the arm and the tab of the housing so that the arm and the tab of the housing slides within the slot as the housing is moved relative to the sleeve, wherein the barb is positioned to engage the tab of the housing to limit movement of the housing relative to the sleeve.

4. The device of claim 3, further comprising a spring configured to move the needle into a retracted state, wherein, upon full introduction of the needle and associated cannula of the subcutaneous infusion device into the subcutaneous layer of skin of the patient, the spring automatically moves the needle into the internal cavity of the housing into the retracted state while leaving the cannula of the subcutaneous infusion device in the subcutaneous layer of skin of the patient.

5. The device of claim 1, further comprising a spring configured to move the needle into a retracted state, wherein, upon full introduction of the needle and associated cannula of the subcutaneous infusion device into the subcutaneous layer of skin of the patient, the spring automatically moves the needle into the internal cavity of the housing into the retracted state while leaving the cannula of the subcutaneous infusion device in the subcutaneous layer of skin of the patient.

6. The device of claim 1, further comprising:
a needle hub disposed in the housing to support the needle; and
a retracting member surrounding at least a portion of the needle hub and configured to retract the needle hub into the housing.

7. The device of claim 6, wherein the retracting member retracts the needle hub into the housing by torsion from extension of the retracting member.

8. The device of claim 1, wherein the sleeve comprises a continuous surface, and wherein the rail and the slot are immediately adjacent one another on the same continuous surface.

9. The device of claim 1, wherein the housing further comprises an arm including a tab extending from the open end.

10. The device of claim 1, wherein the sleeve includes a circumferential inner surface, and wherein the rail and the slot are immediately adjacent one another on the same circumferential inner surface.

11. The device of claim 1, wherein the rail protrudes from the surface.

12. A device for inserting a needle used to introduce a cannula of a subcutaneous infusion device into a subcutaneous layer of skin of a patient, the device comprising:
a housing including a closed end, an open end, and defining an internal cavity, the housing including a threaded portion positioned adjacent to the open end, the threaded portion extending towards the closed end of the housing;
a sleeve configured to be placed against the patient's skin to introduce the cannula into the patient's skin, the sleeve defining a slot extending along a length of the sleeve, at least one rail extending parallel to a centerline of the sleeve on the same surface as the slot, and a barb positioned adjacent to an end of the slot;
the needle positioned within the internal cavity of the housing and coupled to the cannula of the subcutaneous infusion device; and
a cap including a cap closed end and a cap open end, the cap including a cap threaded portion positioned adjacent to the cap open end;
wherein the cap threaded portion is coupled to the threaded portion of the housing with the device in a ship state,
wherein the slot extends along an entire axial length of the sleeve.

13. The device of claim 12, wherein the rail protrudes from the surface.

14. The device of claim 12, wherein the threaded portion of the housing is positioned externally.

15. The device of claim 12, wherein the housing further includes an arm including a tab extending from the open end,
wherein the slot is sized to receive at least a portion of the arm and the tab of the housing so that the arm and the tab of the housing slides within the slot as the housing is moved relative to the sleeve,
wherein the barb is positioned to engage the tab of the housing to limit movement of the housing relative to the sleeve.

16. The device of claim 15, further comprising a spring configured to move the needle into a retracted state, wherein, upon full introduction of the needle and associated cannula of the subcutaneous infusion device into the subcutaneous layer of skin of the patient, the spring automatically moves the needle into the internal cavity of the housing into the retracted state while leaving the cannula of the subcutaneous infusion device in the subcutaneous layer of skin of the patient.

17. The device of claim 12, further comprising a spring configured to move the needle into a retracted state, wherein, upon full introduction of the needle and associated cannula of the subcutaneous infusion device into the subcutaneous layer of skin of the patient, the spring automatically moves the needle into the internal cavity of the housing into the retracted state while leaving the cannula of the subcutaneous infusion device in the subcutaneous layer of skin of the patient.

18. The device of claim 12, further comprising:
a needle hub disposed in the housing to support the needle; and
a retracting member surrounding at least a portion of the needle hub and configured to retract the needle hub into the housing.

19. The device of claim 18, wherein the retracting member retracts the needle hub into the housing by torsion from extension of the retracting member.

20. The device of claim 12, wherein the housing further comprises an arm including a tab extending from the open end.

* * * * *